United States Patent
McDonell et al.

(10) Patent No.: US 11,166,845 B2
(45) Date of Patent: Nov. 9, 2021

(54) ULTRASONIC VITREOUS CUTTING TIP

(71) Applicant: Alcon Inc., Fribourg (CH)

(72) Inventors: Brian William McDonell, Irvine, CA (US); Mikhail Ovchinnikov, Dana Point, CA (US); Yen-Cheng Chen, Orange, CA (US); David Dyk, Foothill Ranch, CA (US); Guangyao Jia, Irvine, CA (US); Mauricio Jochinsen, Fountain Valley, CA (US); Omeed Paydar, Irvine, CA (US); Satish Yalamanchili, Irvine, CA (US)

(73) Assignee: Alcon Inc., Fribourg (CH)

( * ) Notice: Subject to any disclaimer, the term of this patent is extended or adjusted under 35 U.S.C. 154(b) by 229 days.

(21) Appl. No.: 16/366,425

(22) Filed: Mar. 27, 2019

(65) Prior Publication Data
US 2019/0298571 A1   Oct. 3, 2019

Related U.S. Application Data

(60) Provisional application No. 62/652,142, filed on Apr. 3, 2018.

(51) Int. Cl.
*A61F 9/007* (2006.01)
*A61B 17/32* (2006.01)

(52) U.S. Cl.
CPC ........... *A61F 9/00745* (2013.01); *A61B 2017/320073* (2017.08)

(58) Field of Classification Search
CPC .......... A61F 9/00745; A61F 9/00709; A61F 9/0133; A61B 2017/320073; A61B 2017/320098; A61B 2017/32007; A61B 2017/32008; A61B 2017/320074; A61B 7/320068; A61B 2017/00402; A61B 2017/320004; A61B 2017/320024; A61B 2017/320028; A61B 2017/320071; A61B 2017/320078; A61B 2017/320082; A61B 2017/320084; A61B 2017/320089;
(Continued)

(56) References Cited

U.S. PATENT DOCUMENTS

| 3,805,787 A | 4/1974 | Banko |
| 3,941,122 A | 3/1976 | Jones |

(Continued)

FOREIGN PATENT DOCUMENTS

| RU | 2685902 C1 * | 4/2019 |
| WO | WO9305718 A1 | 4/1993 |

(Continued)

OTHER PUBLICATIONS

Alcon, Alcon 2012 Cataract and Refractive Product Catalog, 2012 (83 pages).
(Continued)

*Primary Examiner* — Tan-Uyen T Ho
*Assistant Examiner* — Arwa Mostafa

(57) ABSTRACT

An ultrasonic cutting tip has a hollow shaft with a proximal and distal end. The proximal end is configured to be attached to an ultrasonic hand piece, and the distal end has a smooth continuous surface. An opening is located near the distal end of the hollow shaft. The opening is configured to cut vitreous when the cutting tip is vibrated ultrasonically in a torsional manner.

20 Claims, 10 Drawing Sheets

(58) Field of Classification Search
CPC .. A61B 2018/0019; A61B 2018/00202; A61B 2017/320069; A61B 2017/320072; A61B 2017/320075; A61B 2017/320077
See application file for complete search history.

(56) References Cited

U.S. PATENT DOCUMENTS

| | | | |
|---|---|---|---|
| 4,428,748 | A | 1/1984 | Peyman |
| 4,531,934 | A | 7/1985 | Kossovsky et al. |
| 4,750,902 | A | 6/1988 | Wuchinich |
| 4,989,583 | A | 2/1991 | Hood |
| 5,772,627 | A | 6/1998 | Acosta |
| 6,007,513 | A | 12/1999 | Anis et al. |
| 6,126,629 | A | 10/2000 | Perkins |
| 6,159,175 | A | 12/2000 | Strukel et al. |
| 6,270,471 | B1 | 8/2001 | Hechel |
| 6,402,769 | B1 | 6/2002 | Boukhny |
| 7,651,490 | B2 | 1/2010 | Boukhny et al. |
| 8,016,843 | B2 | 9/2011 | Escaf |
| 8,308,735 | B2 | 11/2012 | Dimalanta |
| 8,403,951 | B2 | 3/2013 | Chon |
| 8,579,929 | B2 | 11/2013 | Mackool |
| 8,888,802 | B2 | 11/2014 | Underwood |
| 9,095,409 | B2 | 8/2015 | Underwood |
| 9,101,441 | B2 | 8/2015 | Underwood |
| 9,233,021 | B2 | 1/2016 | Artsyukhovich |
| 9,278,027 | B2 | 3/2016 | Sussman |
| 9,498,377 | B2 | 11/2016 | Mccary |
| 10,258,505 | B2 | 4/2019 | Ovchinnikov |
| 2001/0011176 | A1 | 8/2001 | Boukhny |
| 2005/0021065 | A1* | 1/2005 | Yamada ......... A61B 17/320068 606/169 |
| 2006/0189948 | A1 | 8/2006 | Boukhny |
| 2006/0206050 | A1 | 9/2006 | Chon |
| 2006/0253056 | A1 | 11/2006 | Kadziauskas |
| 2007/0185514 | A1 | 8/2007 | Kirchhevel |
| 2007/0255196 | A1 | 11/2007 | Wuchinich |
| 2007/0260173 | A1 | 11/2007 | Boukhny |
| 2007/0260200 | A1 | 11/2007 | Boukhny |
| 2009/0190003 | A1 | 7/2009 | Park |
| 2010/0036256 | A1 | 2/2010 | Boukhny |
| 2011/0112466 | A1 | 5/2011 | Dimalanta |
| 2011/0196286 | A1* | 8/2011 | Robertson ...... A61B 17/320758 604/22 |
| 2012/0157912 | A1 | 6/2012 | Sorensen |
| 2013/0226152 | A1 | 8/2013 | Zolli |
| 2014/0074013 | A1 | 3/2014 | Mccary |
| 2014/0171997 | A1 | 6/2014 | Nissan |
| 2014/0364886 | A1 | 12/2014 | Underwood |
| 2015/0173948 | A1 | 6/2015 | Heeren |
| 2016/0100982 | A1 | 4/2016 | Mccary |
| 2019/0008680 | A1 | 1/2019 | Jochinsen |

FOREIGN PATENT DOCUMENTS

| | | |
|---|---|---|
| WO | WO0000096 A1 | 1/2000 |
| WO | WO2011151837 A1 | 12/2011 |
| WO | WO2015158438 A1 | 10/2015 |

OTHER PUBLICATIONS

Alcon, Alcon Vitreoretinal Product Catalog 2014, 2014 (62 pages).

* cited by examiner

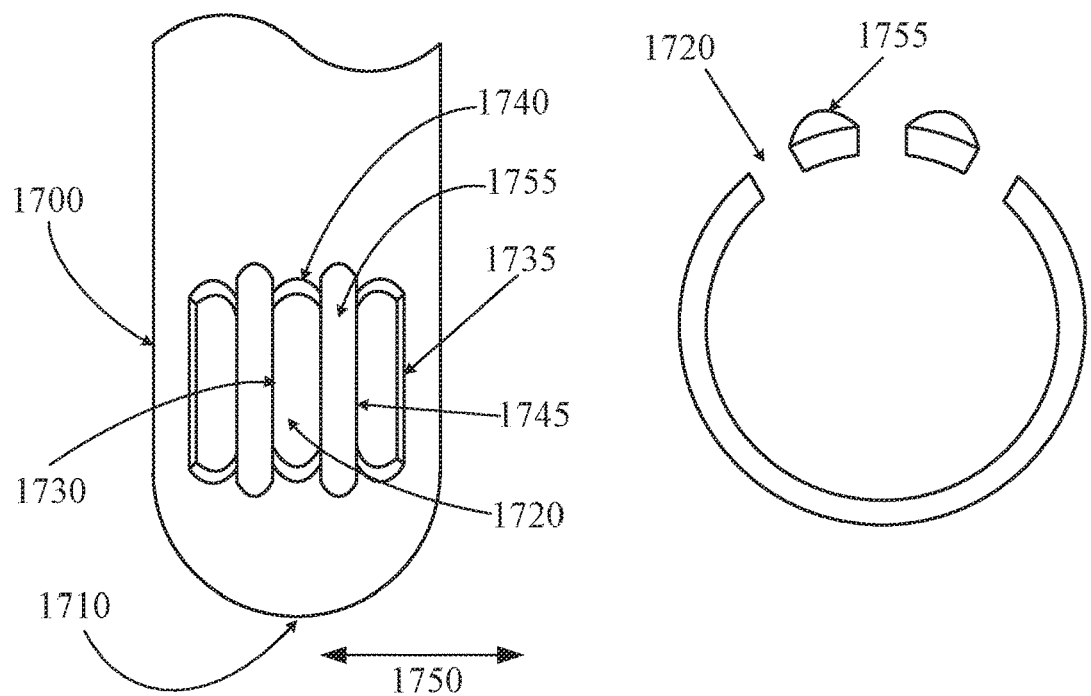
Fig. 17A
Fig. 17B
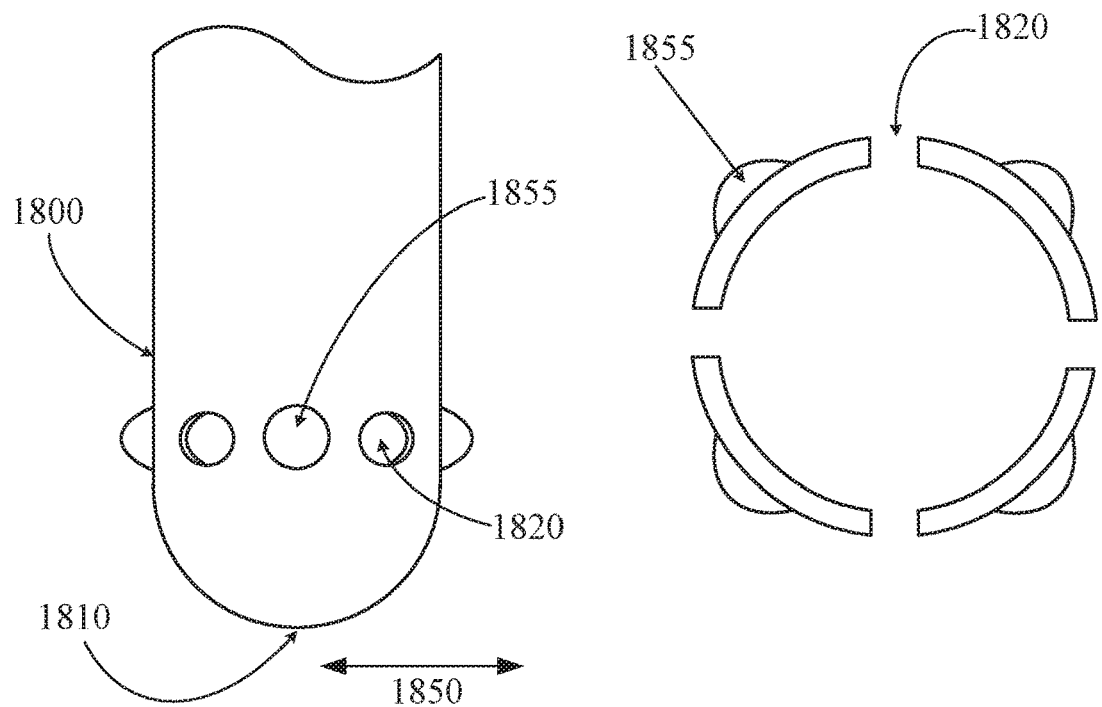
Fig. 18A
Fig. 18B

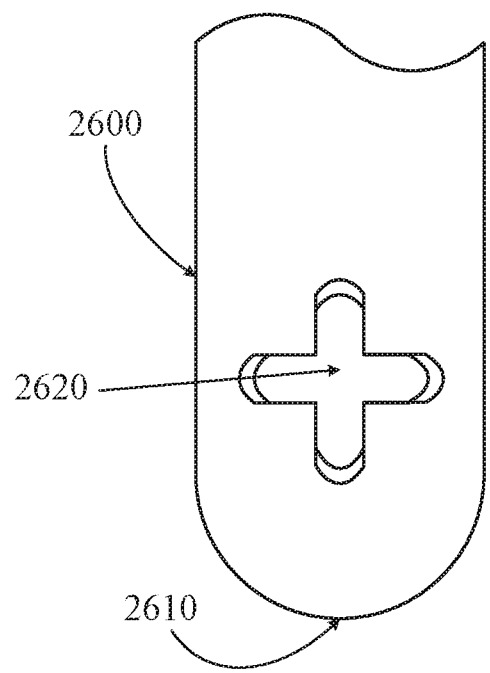
Fig. 26
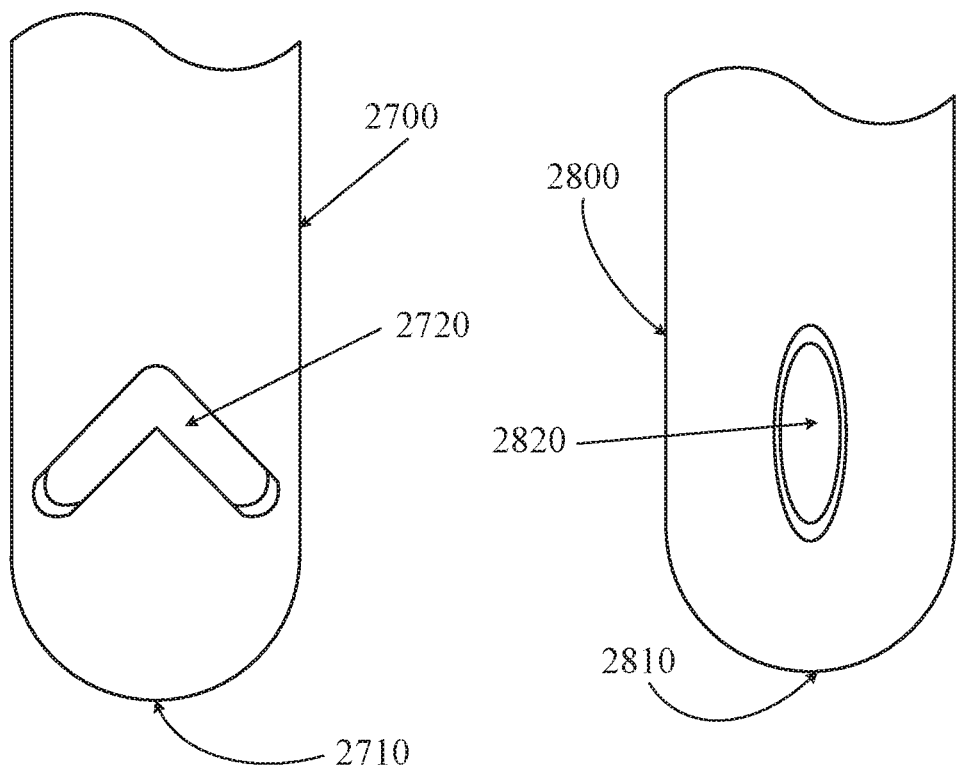
Fig. 27
Fig. 28

ULTRASONIC VITREOUS CUTTING TIP

PRIORITY CLAIM

This application claims the benefit of priority of U.S. Provisional Patent Application Ser. No. 62/652,142 titled "Ultrasonic Vitreous Cutting Tip," filed on Apr. 3, 2018, whose inventors are listed as Brian William McDonell and Mikhail Ovchinnikov, which is hereby incorporated by reference in its entirety as though fully and completely set forth herein.

BACKGROUND OF THE INVENTION

The present invention relates to an ophthalmic surgical device for the removal of vitreous from an eye, and more particularly to probe tips designed to be ultrasonically vibrated to remove vitreous.

Anatomically, the eye is divided into two distinct parts—the anterior segment and the posterior segment. The anterior segment includes the lens and extends from the outermost layer of the cornea (the corneal endothelium) to the posterior of the lens capsule. The posterior segment includes the portion of the eye behind the lens capsule. The posterior segment extends from the anterior hyaloid face to the retina, with which the posterior hyaloid face of the vitreous body is in direct contact. The posterior segment is much larger than the anterior segment.

The posterior segment includes the vitreous body—a clear, colorless, gel-like substance. It makes up approximately two-thirds of the eye's volume, giving it form and shape before birth. It is composed of 1% collagen and sodium hyaluronate and 99% water. The anterior boundary of the vitreous body is the anterior hyaloid face, which touches the posterior capsule of the lens, while the posterior hyaloid face forms its posterior boundary, and is in contact with the retina. The vitreous body is not free-flowing like the aqueous humor and has normal anatomic attachment sites. One of these sites is the vitreous base, which is a 3-4 mm wide band that overlies the or a serrata. The optic nerve head, macula lutea, and vascular arcade are also sites of attachment. The vitreous body's major functions are to hold the retina in place, maintain the integrity and shape of the globe, absorb shock due to movement, and to give support for the lens posteriorly. In contrast to aqueous humor, the vitreous body is not continuously replaced. The vitreous body becomes more fluid with age in a process known as syneresis. Syneresis results in shrinkage of the vitreous body, which can exert pressure or traction on its normal attachment sites. If enough traction is applied, the vitreous body may pull itself from its retinal attachment and create a retinal tear or hole.

Various surgical procedures, called vitreo-retinal procedures (or retinal procedures), are commonly performed in the posterior segment of the eye. Vitreo-retinal procedures are appropriate to treat many serious conditions of the posterior segment. Vitreo-retinal procedures treat conditions such as age-related macular degeneration (AMD), diabetic retinopathy and diabetic vitreous hemorrhage, macular hole, retinal detachment, epiretinal membrane, CMV retinitis, and many other ophthalmic conditions.

A surgeon performs vitreo-retinal procedures with a microscope and special lenses designed to provide a clear image of the posterior segment. Several tiny incisions just a millimeter or so in length are made on the sclera at the pars plana. The surgeon inserts microsurgical instruments through the incisions such as a fiber optic light source to illuminate inside the eye, an infusion line to maintain the eye's shape during surgery, and instruments to cut and remove the vitreous body (such as a vitrectomy probe—which includes a small gauge needle or cannula with a cutting mechanism on the end that is inserted into the eye).

The surgical machine used to perform a vitrectomy and other surgeries on the posterior of the eye is very complex. Typically, such an ophthalmic surgical machine includes a main console to which the numerous different tools are attached. The main console provides power to and controls the operation of the attached tools.

The attached tools typically include probes, scissors, forceps, illuminators, vitrectors, and infusion lines. Each of these tools is typically attached to the main surgical console. A computer in the main surgical console monitors and controls the operation of these tools. These tools also get their power from the main surgical console. Some of these tools are electrically powered while others are pneumatically powered.

Currently, vitrectomy probes typically include a small blade that reciprocates inside a cannula. In this manner, vitrectomy probes operate like a guillotine cutting tiny pieces of vitreous with each stroke of the blade. Such probe designs are common and operate by cutting tiny pieces of vitreous with each stroke. Since the vitreous is attached to the retina, cutting tiny pieces of vitreous reduces the amount of tugging that occurs on the retina. Typical speeds of a vitrectomy probe can reach 10,000 cuts per minute.

Other methods of removing vitreous have been attempted. One such method is the use of an ultrasonic cutting instrument. Much like in phacoemulsification, a cutting tip can be vibrated ultrasonically to cut vitreous.

The operative part in a typical hand piece is a centrally located, hollow resonating bar or horn directly attached to a set of piezoelectric crystals. The crystals supply the required ultrasonic vibration needed to drive both the horn and the attached cutting tip, and are controlled by the console. The crystal/horn assembly is suspended within the hollow body or shell of the hand piece by flexible mountings. The hand piece body terminates in a reduced diameter portion or nosecone at the body's distal end. Typically, the nosecone is threaded to accept the cutting tip. Likewise, the horn bore is threaded at its distal end to receive the threads of the cutting tip.

During a procedure, the tip of the cutting tip is inserted into the posterior chamber of the eye through a small incision in the outer tissue of the eye. The surgeon brings the cutting tip into contact with vitreous, so that the cutting tip when vibrated cuts or shears the vitreous. The resulting pieces of vitreous are aspirated out of the eye through the interior bore of the cutting tip.

Power is applied to the hand piece to vibrate the cutting tip. In general, the amplitude of tip movement (or vibration) is proportional to the power applied. In conventional hand pieces, the needle vibrates back and forth producing a longitudinal needle stroke. In improved systems, the needle may be caused to vibrate in a twisting or torsional motion which can improve cutting efficiency.

In order to effectively cut vitreous, the cutting tip should be optimized for such an application. It would be desirable to have an ultrasonic cutting tip with a configuration designed to enhance cutting of the vitreous for torsional ultrasonic vibration.

SUMMARY OF THE INVENTION

In one example consistent with the principles of the present invention, the present invention provides an ultrasonic cutting tip comprising: a hollow shaft with a proximal end and a distal end, the proximal end configured to be attached to an ultrasonic hand piece capable of producing torsional vibration along a direction of vibration, and the distal end having a smooth continuous surface, the hollow shaft having a longitudinal axis that extends through an interior lumen of the hollow shaft; an opening located near the distal end of the hollow shaft, the opening having a width and a length, the length being longer than the width; wherein the width of the opening is oriented along the direction of vibration and perpendicular to the longitudinal axis of the hollow shaft.

In another example, the opening is slot-shaped and traverses a wall of the hollow shaft at an oblique angle so as to form a leading edge and a trailing edge along the length of the opening, and further wherein the length of the opening is oriented parallel to the longitudinal axis of the hollow shaft. The distal end of the hollow shaft may also be spherical and the slot-shaped opening traverses the wall of the hollow shaft such that a portion of the slot-shaped opening is traverses the spherical distal end.

In another example, the opening is slot-shaped and traverses a wall of the hollow shaft at a right angle so as to form a leading edge and a trailing edge along the length of the opening, and further wherein the length of the opening is oriented parallel to the longitudinal axis of the hollow shaft. The cutting tip may also include two additional slot-shaped openings that each traverse the wall of the hollow shaft at a right angle, such that a length each of the additional slot-shaped openings is oriented parallel to the longitudinal axis of the hollow shaft. The cutting tip may also include a raised structure located between two of the slot-shaped openings.

In another example, the ultrasonic cutting tip may have an array of openings arranged near a distal end of the hollow shaft, such that each opening in the array of openings traverses a wall of the hollow shaft. The cutting tip may have a raised structure located between two of the openings in the array of openings.

In another example, the opening is oval-shaped. The opening may also have a pair of wires located in the opening.

In another example, a system includes and ultrasonic hand piece and a cutting tip as described above. The ultrasonic hand piece produces torsional vibration, and the cutting tip is adapted to be attached to the hand piece.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 17A is a perspective view of a cutting tip according to the principles of the present invention.

FIG. 17B is a cross section view of the cutting tip shown is FIG. 17A.

FIG. 18A is a perspective view of a cutting tip according to the principles of the present invention.

FIG. 18B is a cross section view of the cutting tip shown is FIG. 18A.

FIG. 26 illustrates a cross-shaped port on a cutting tip.

FIG. 27 illustrates a V-shaped port on a cutting tip.

FIG. 28 is a perspective view of a cutting tip according to the principles of the present invention.

DETAILED DESCRIPTION OF THE PREFERRED EMBODIMENTS

Reference is now made in detail to the exemplary embodiments of the invention, examples of which are illustrated in the accompanying drawings. Wherever possible, the same reference numbers are used throughout the drawings to refer to the same or like parts.

Figure 1:
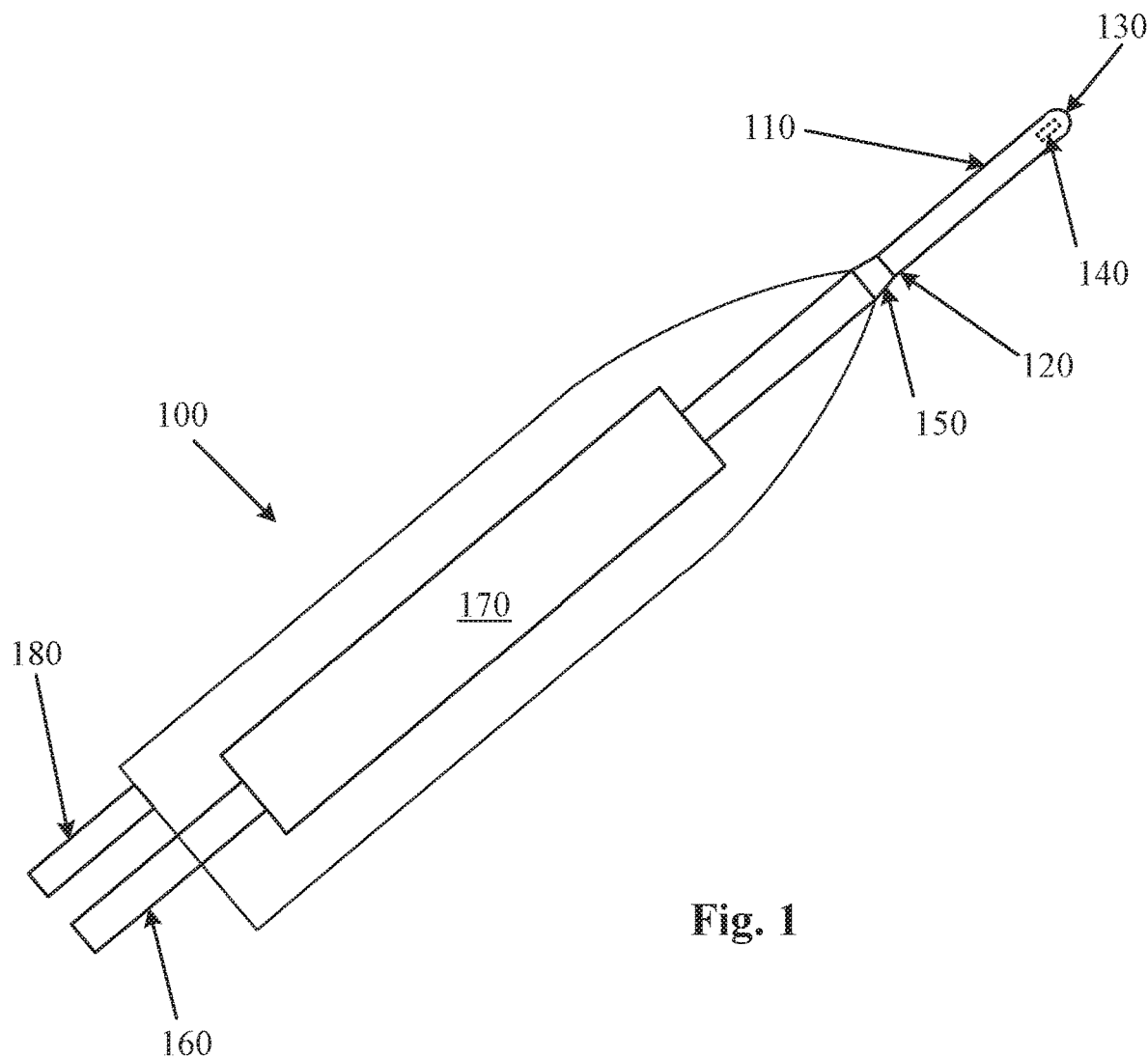
FIG. 1 is a diagram of an ultrasonic hand piece and attached cutting tip according to the principles of the present invention.

In one example of the present invention, FIG. 1 shows a hand piece 100, such as an ultrasonic hand piece, attached to a cutting tip 110. The cutting tip has a proximal end 120 and a distal end 130. The proximal end 120 of the cutting tip 110 is configured to be attached to a hub 150 of the hand piece 100. In one example, the proximal end of the cutting tip 120 and the hub are threaded so that the proximal end 120 of the cutting tip 110 can be secured to the hub 150. The distal end 130 of cutting tip 110 is smooth. For example, the distal end 130 may be rounded, spherical, or have a smooth continuous surface. An opening 140 is located near the distal end 130. The opening 140 has a width and a length as shown in more detail in subsequent drawings. The cutting tip 110 is hollow such that the opening 140 communicates with the hollow interior of the cutting tip 110. The hollow interior of the cutting tip 110 allows for materials, such as vitreous, to be aspirated from the eye through opening 140 and the hollow interior of the cutting tip 110.

In the example of FIG. 1, hand piece 100 includes an aspiration conduit 160, a driver 170, and an optional irrigation conduit 180. Aspiration conduit 160 extends from the hub 150, through or around the driver 170, and out of the end of the hand piece 110. Aspiration conduit 160 is coupled to the hollow interior of cutting tip 110 such that a continuous aspiration pathway is formed. Material, such as vitreous, can be aspirated through opening 140, aspiration conduit 160, and out of hand piece 110. Driver 170, which may include a set of piezoelectric crystals coupled to a horn, produces vibrations. Driver 170 is rigidly coupled to cutting tip 110 via hub 150 and aspiration conduit 160. When driver 170 vibrates, cutting tip 110 also vibrates. In this manner, driver 170 induces vibrations in cutting tip 110. For example, driver 170 may produce longitudinal vibrations, torsional vibrations, transverse vibrations or vibrations in another direction or orientation. Cutting tip 110 will vibrate in a like manner. An optional irrigation conduit 180 provides irrigation fluid to the eye.

In one example, the driver 170 produces torsional or twisting motion at the end of cutting tip with opening 140. In this manner, the opening 140 sweeps back and forth or twists while contacting vitreous. This twisting or sweeping motion has been found to more effectively cuts vitreous than a traditional longitudinal motion. (Traditional ultrasonic hand pieces produces longitudinal vibration of the cutting tip that results in a jack hammer type motion as the tip moves along its longitudinal axis). This torsional movement is shown in more detail in the subsequent drawings. Generally, the cutting tips disclosed in the following drawings are designed to take advantage of the torsional, twisting, or sweeping motion to cut vitreous. Because of the motion of the edges of the opening, the rotational or torsional motion of the cutting tip will result in lateral motion of the fluid within the opening. The boundary layer of the fluid around the periodically vibrating cutting tip is relatively thin. This results in a high velocity gradient between the moving fluid in the opening and the stationary fluid beyond the boundary layer. This causes a shearing motion of vitreous or other materials aspirated into the opening. In addition, interaction with the edges of the opening also cause a shearing action.

Figure 2:
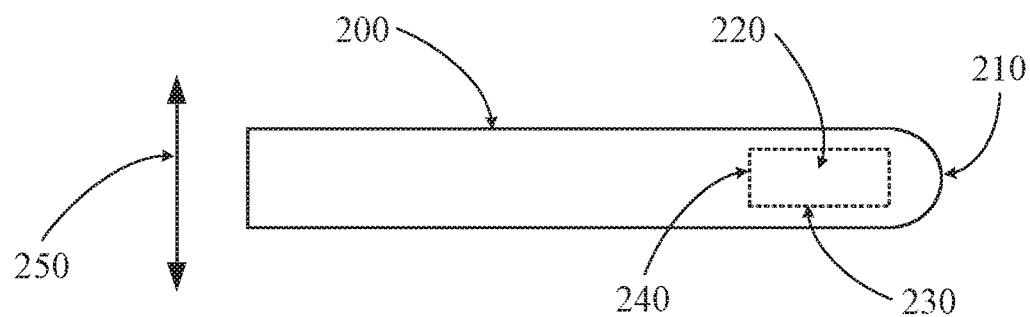
FIG. 2 is a view of a generic cutting tip according to the principles of the present invention.

FIG. 2 is a view of a cutting tip according to the principles of the present invention. In the example of FIG. 2, cutting tip 200 is a hollow shaft with a rounded distal end 210. An opening 220 is located near the distal end 210 of cutting tip 200. Opening 220 has a length 230 and a width 240. In this case, the length 230 is longer than the width 240. Opening 220 is in fluid communication with the hollow interior of cutting tip 200. Opening 220 and the hollow interior of cutting tip 200 form a part of an aspiration pathway.

The arrow 250 shows the direction that the tip 200 is vibrated. In this case, the direction of vibration is generally along or parallel to the width 240 of the opening 220 (and generally perpendicular or normal to the length 230 of the opening 220). When inserted into the posterior chamber of the eye and vibrated in this manner, the length 230 of opening 220 is moved perpendicular to the direction of vibration. The edge of the opening defined by the length 230 is moved across vitreous in order to shear or cut it. In operation, an aspiration source, such as a pump, is fluidly coupled through the hand piece to the interior hollow lumen of cutting tip 200. Vitreous is drawn into opening 220 by this aspiration source. As vitreous is drawn into opening 220, the cutting tip 200 is vibrated, typically ultrasonically, so that the edge defined by the length 230 of opening 220 cuts or shears the vitreous. During each stroke of vibration, vitreous drawn into opening 220 is contacted by the edge of opening 220 along the length 230. In this manner, the longer edges of opening 220 are used to cut vitreous. Once cut, the vitreous is aspirated out of the eye through the hollow interior lumen of cutting tip 200.

Figure 3A:
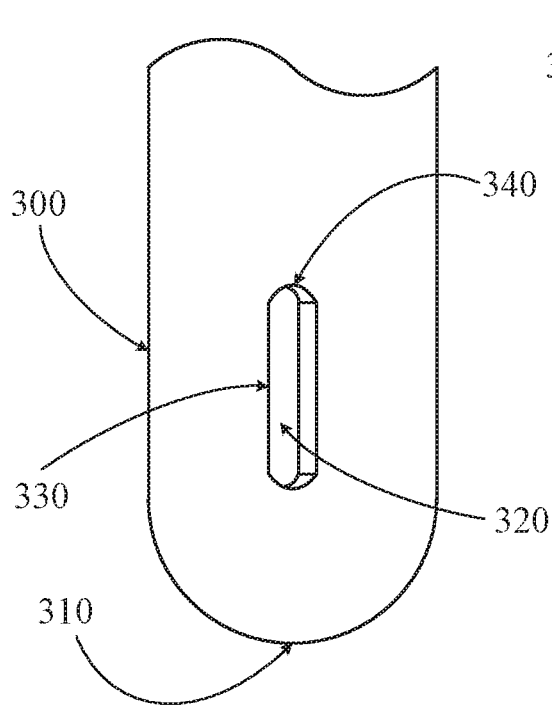
FIG. 3A is a perspective view of a cutting tip according to the principles of the present invention.
Figure 3B:
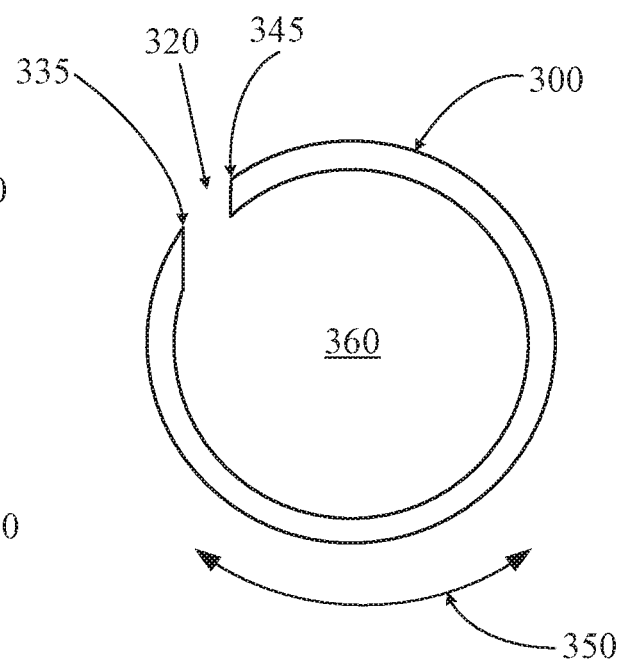
FIG. 3B is a cross section view of the cutting tip shown is FIG. 3A.

FIG. 3A is a perspective view of a cutting tip according to the principles of the present invention. FIG. 3B is a cross section view of the cutting tip shown is FIG. 3A. In this example, cutting tip 300 is a hollow shaft with a rounded distal end 310. An opening 320 is located near the distal end 310 of cutting tip 300. Opening 320 has a length 330 and a width 340. In this case, the length 330 is longer than the width 340. Opening 320 is in fluid communication with the hollow interior of cutting tip 300. Opening 320 and the hollow interior lumen 360 of cutting tip 300 form a part of an aspiration pathway. Opening 320 is a slot-shaped opening that pierces the wall of cutting tip 300 at an angle as shown in FIG. 3B. In this manner, a leading edge 335 is formed that transverse a longer portion of the wall of cutting tip 300 than does a trailing edge 345 that transverses a shorter wall length. Both the leading edge 335 and trailing edge 345 of opening 320 cut vitreous as the cutting tip 300 is vibrated.

The arrow 350 shows the direction that the tip 300 is vibrated. In this case, the direction of vibration is generally rotational, twisting, or torsional along or parallel to the width 340 of the opening 320 (and generally perpendicular or normal to the length 330 of the opening 320). When inserted into the posterior chamber of the eye and vibrated in this manner, the length 330 of opening 320 is moved perpendicular to the direction of vibration. The edges 335 and 345 of the opening 320 (i.e. the edges along the length 330) are moved across vitreous in order to shear or cut it. In operation, an aspiration source, such as a pump, is fluidly coupled through the hand piece to the interior hollow lumen of cutting tip 300. Vitreous is drawn into opening 320 by this aspiration source. As vitreous is drawn into opening 320, the cutting tip 300 is vibrated, typically ultrasonically, so that the edges 335 and 345 defined by the length 330 of opening 320 cuts or shears the vitreous. During each stroke of vibration, vitreous drawn into opening 320 is contacted by the edges 335 and 345 of opening 320 along the length 330. In this manner, the longer edges of opening 320 are used to cut vitreous. Once cut, the vitreous is aspirated out of the eye through the hollow interior lumen 360 of cutting tip 330. The leading edge 335 of opening 320 is generally sharper than the trailing edge 345 because of the angle of opening 320 in the wall of cutting tip 300.

Figure 4A:
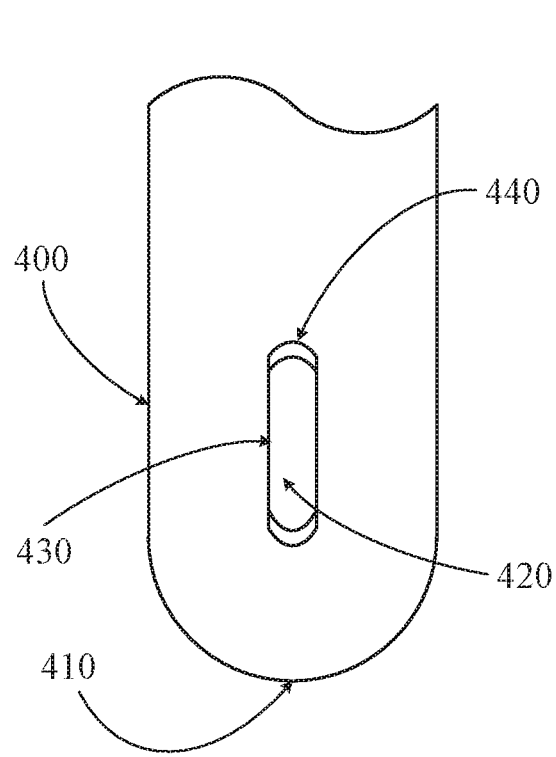
FIG. 4A is a perspective view of a cutting tip according to the principles of the present invention.
Figure 4B:
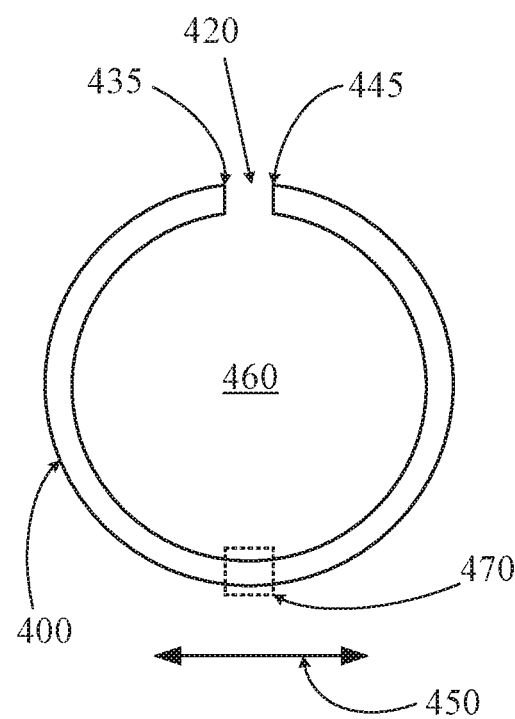
FIG. 4B is a cross section view of the cutting tip shown is FIG. 4A.

FIG. 4A is a perspective view of a cutting tip according to the principles of the present invention. FIG. 4B is a cross section view of the cutting tip shown is FIG. 4A. In this example, cutting tip 400 is a hollow shaft with a rounded distal end 410. An opening 420 is located near the distal end 410 of cutting tip 400. Opening 420 has a length 430 and a width 440. In this case, the length 430 is longer than the width 440. Opening 420 is in fluid communication with the hollow interior of cutting tip 400. Opening 420 and the hollow interior lumen 460 of cutting tip 400 form a part of an aspiration pathway. Opening 420 is a slot-shaped opening that pierces the wall of cutting tip 400 as shown in FIG. 3B. In this manner, a leading edge 435 is formed that transverse a portion of the wall of cutting tip 400 that is approximately the same length as the wall length traversed by trailing edge 445. Both the leading edge 435 and trailing edge 445 of opening 420 cut vitreous as the cutting tip 400 is vibrated.

The arrow 450 shows the direction that the tip 400 is vibrated. In this case, the direction of vibration is generally rotational, twisting, or torsional along or parallel to the width 440 of the opening 420 (and generally perpendicular or normal to the length 430 of the opening 420). When inserted into the posterior chamber of the eye and vibrated in this manner, the length 430 of opening 420 is moved perpendicular to the direction of vibration. The edges 435 and 445 of the opening 420 (i.e. the edges along the length 430) are moved across vitreous in order to shear or cut it. In operation, an aspiration source, such as a pump, is fluidly coupled through the hand piece to the interior hollow lumen of cutting tip 400. Vitreous is drawn into opening 420 by this aspiration source. As vitreous is drawn into opening 420, the cutting tip 400 is vibrated, typically ultrasonically, so that the edges 435 and 445 defined by the length 430 of opening 420 cuts or shears the vitreous. During each stroke of vibration, vitreous drawn into opening 420 is contacted by the edges 435 and 445 of opening 420 along the length 430. In this manner, the longer edges of opening 420 are used to cut vitreous. Once cut, the vitreous is aspirated out of the eye through the hollow interior lumen 460 of cutting tip 400.

Other openings, such as opening 470 may also be present. In this example, a second opening 470 is located opposite opening 420. Opening 470 has the same geometry as opening 420. If opening 470 is present, then two additional cutting edges (like edges 435 and 445) are present to cut vitreous. While two openings are described, any number of openings may be present as more clearly described below.

Figure 5A:
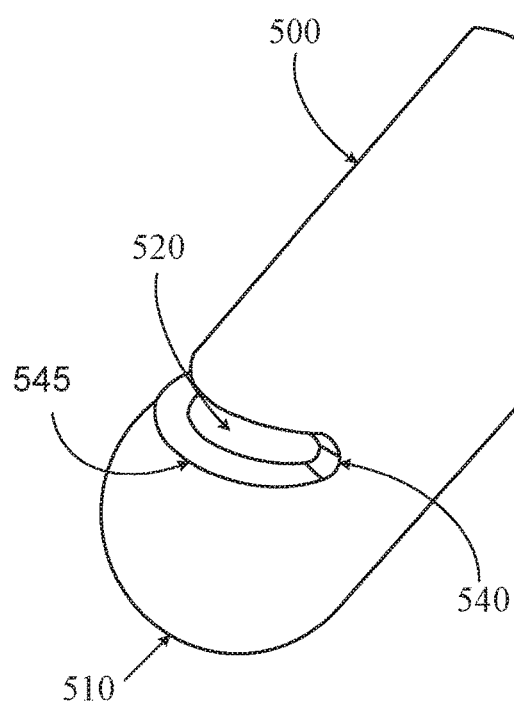
FIG. 5A is a perspective view of a cutting tip for longitudinal actuation.
Figure 5B:
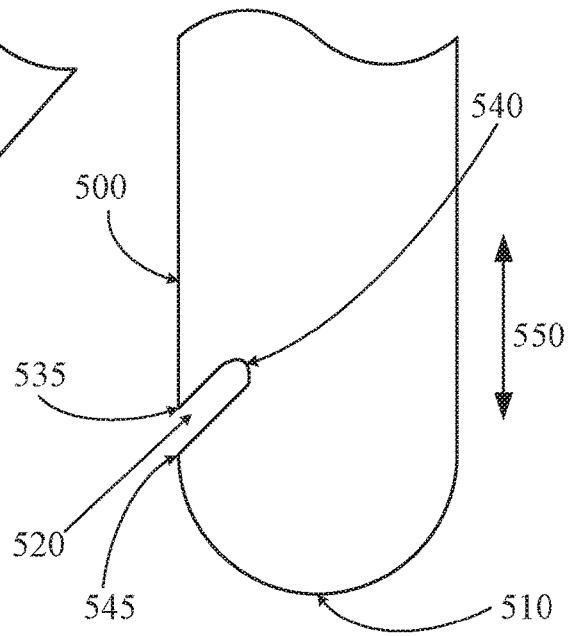
FIG. 5B is a side view of the cutting tip shown in FIG. 5A.

FIG. 5A is a perspective view of a cutting tip 500 for longitudinal actuation 550. FIG. 5B is a side view of the cutting tip 500 shown in FIG. 5A. FIGS. 5A-B may be similar to FIG. 6 except the geometry of the cutting port 520 in tip 500 may result in sharper corners on both the proximal (535) and distal (545) edges where the vitreous interacts during the cuts. Side edge 540 may connect the proximal (535) and distal (545) edges. Cutting tip 500 may include a distal end 510.

Figure 6A:
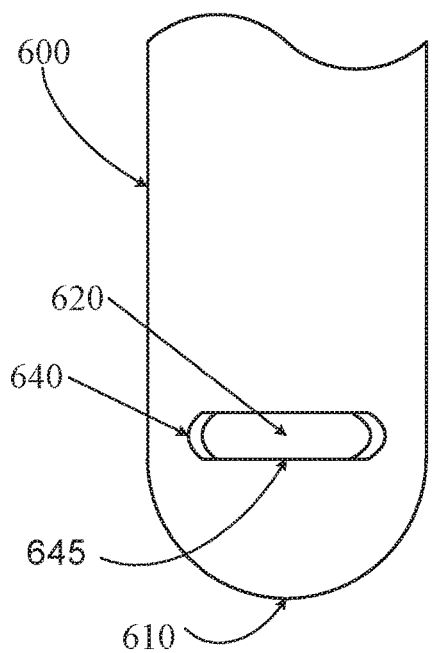
FIG. 6A is a perspective view of another cutting tip geometry for longitudinal actuation.
Figure 6B:
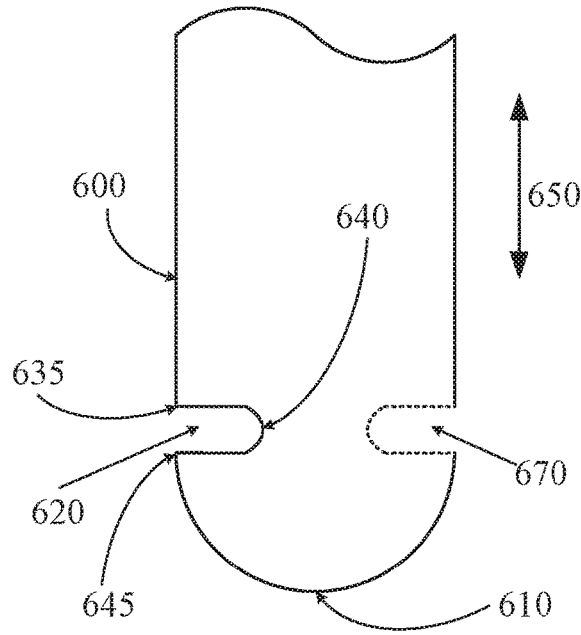
FIG. 6B is a side view of the cutting tip shown in FIG. 6A.

FIG. 6A is a perspective view of another cutting tip 600 for longitudinal actuation 650. FIG. 6B is a side view of the cutting tip 600 shown in FIG. 6A. FIGS. 6A-B show a horizontal slot shaped port 620. Compared to a round hole, this horizontal slot port 620 results in more vitreous interaction with the edges 635,645 (i.e. the vitreous is forced to flow closer to the edges 635,645 as it passes through the port 620 resulting in more shearing). Side edge 640 may connect the proximal (635) and distal (645) edges. Cutting tip 600 may include a distal end 610. Dashed port 670 shows the location of an optional second horizontal slot on the same tip 600.

Figure 7A:
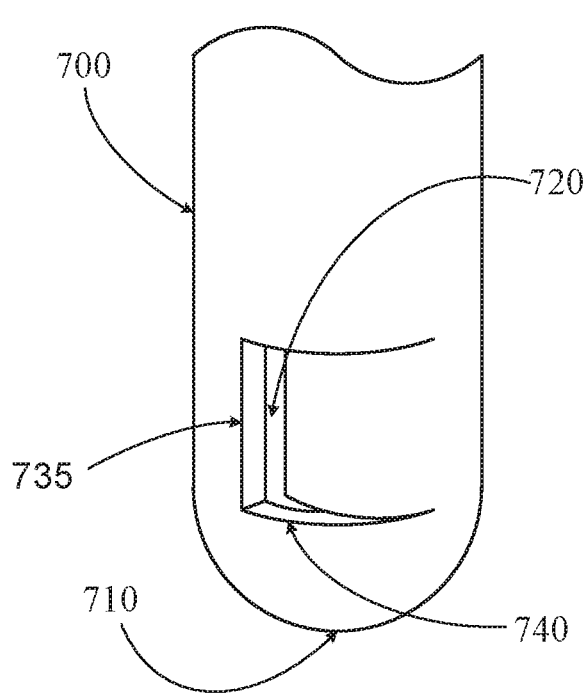
FIG. 7A is a perspective view of a cutting tip for torsional actuation.
Figure 7B:
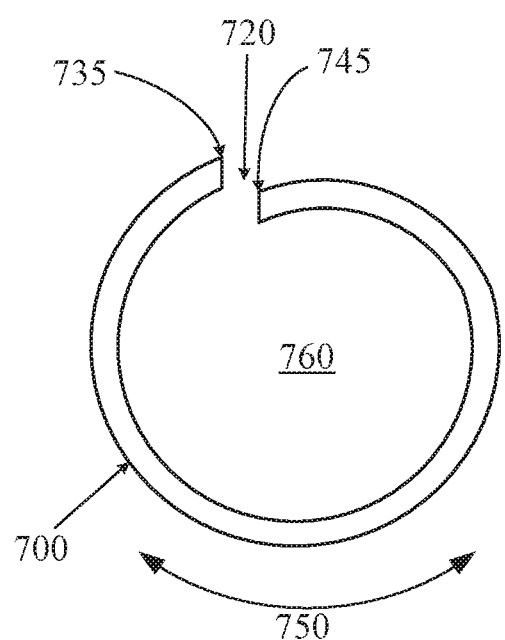
FIG. 7B is a cross section view of the cutting tip shown is FIG. 7A.

FIG. 7A is a perspective view of a cutting tip 700 for torsional actuation 750. FIG. 7B is a cross section view of the cutting tip shown is FIG. 7A. The offset, vertical slot shaped port 720 causes shearing interaction with the vitreous when exposed to torsional actuation. Shearing forces may be produced, for example, between edges 735, 745 and the vitreous to cut the vitreous as the vitreous enters port 720 to be aspirated into lumen 760. Side edge 740 may not cut the vitreous in a torsional mode. Cutting tip 700 may include a distal end 710.

Figure 8A:
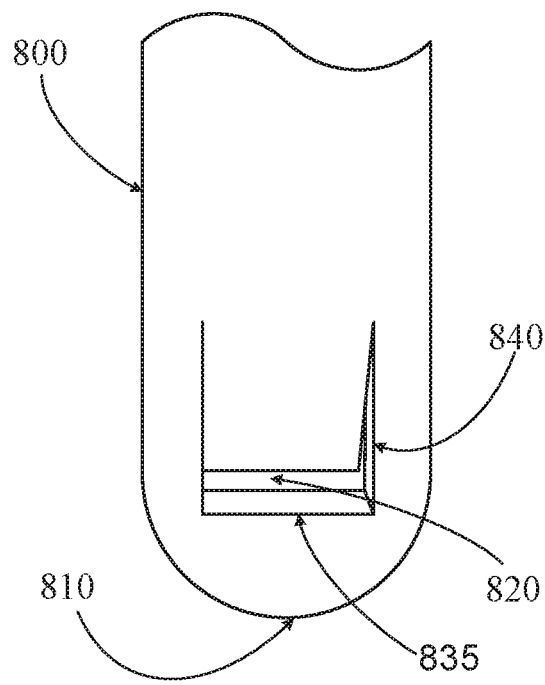
FIG. 8A is a perspective view of another cutting tip geometry for longitudinal actuation.
Figure 8B:
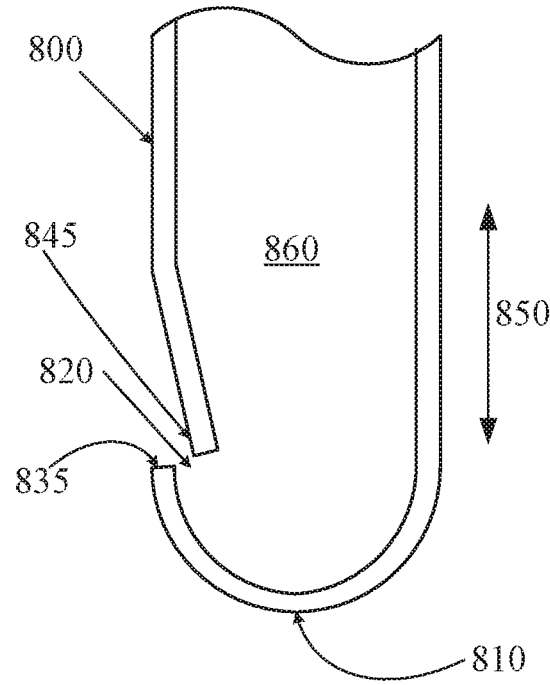
FIG. 8B is a side view of the cutting tip shown in FIG. 6A.

FIG. 8A is a perspective view of another cutting tip 800 for longitudinal actuation 850. FIG. 8B is a side view of the cutting tip 800 shown in FIG. 8A. FIGS. 8A-B show a horizontally arranged slot shaped port 820. The offset, horizontal slot shaped port 820 causes shearing interaction with the vitreous when exposed to longitudinal actuation 850. Shearing forces may be produced, for example, between the vitreous and edge 835 and an edge on the end of lip 845 to cut the vitreous as the vitreous enters port 820 to be aspirated into lumen 860. Side edge 840 may not cut the vitreous in a torsional mode. Side edge 840 may connect the proximal (835) and distal (845) edges. Cutting tip 800 may include a distal end 810.

Figure 9:
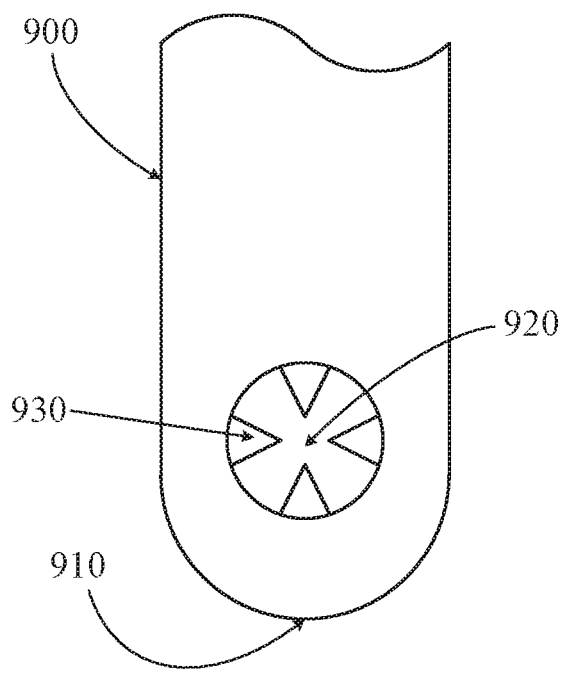
FIG. 9 shows a star-shaped port on a cutting tip.

FIG. 9 shows a star-shaped port 920 on a cutting tip 900. The sharpening star shaped port 920 on an inner wall may be configured to grab vitreous fibers. Since the vitreous fibers may be somewhat held by the port geometry, a cutting efficiency between the port edges (e.g., edges on teeth 930 and between the teeth 930) and the vitreous fibers may be increased. Cutting tip 900 may have a distal end 910. The "dentata" (or perhaps better, "sea lamprey") design seeks to create an orifice with an array of sharp teeth 930 around the circumference of a circular port opening 920 that facilitate vitreous cutting as the tip 900 rotates or translates with respect to the surrounding vitreous. The many small teeth 930 may be more likely to be in the right position to tear the vitreous at any given time during the actuation and position than a single blade might be.

Figure 10:
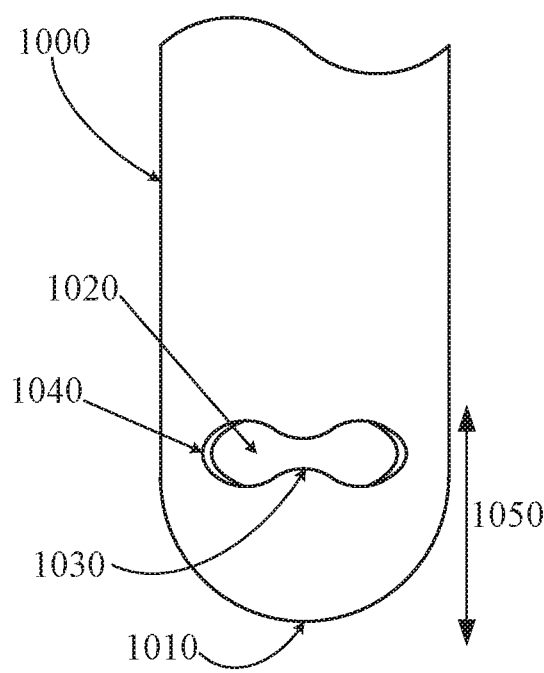
FIG. 10 shows an hourglass shaped port on a cutting tip.

FIG. 10 shows an hourglass shaped port 1020 on a cutting tip 1000. The "hourglass" shaped port 1020 is aimed at offering an aperture shape with enhanced cutting capability due to the constrictions of two different size holes (forming the hourglass shape) that are spaced close together. For example, distal edge 1030 may cut vitreous during a longitudinal actuation 1050 while side edge 1040 may cut vitreous during a torsional motion. Cutting tip 1000 may have a distal end 1010.

Figure 11:
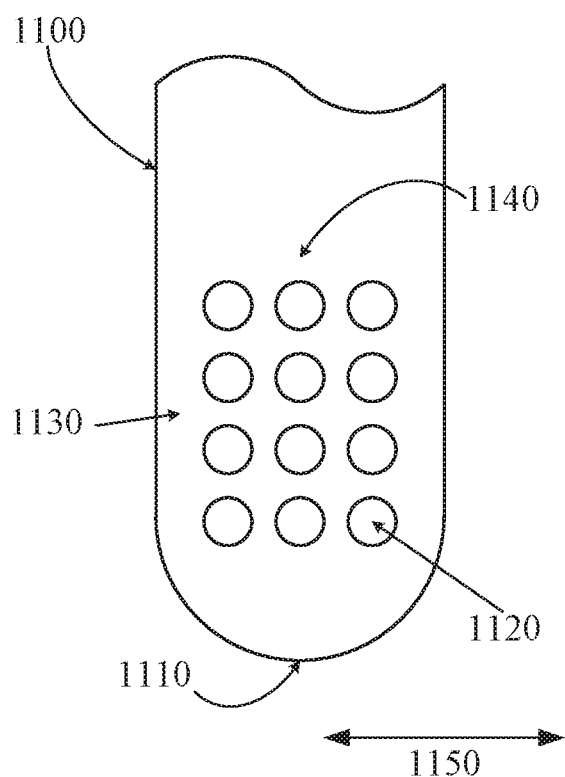
FIG. 11 is a perspective view of a cutting tip according to the principles of the present invention.

FIG. 11 is a front view of a cutting tip according to the principles of the present invention. A plurality of openings 1120 are located near the distal end 1110 of cutting tip 1100. The set of openings 1120 have a length 1130 and a width 1140. In this case, the total length 1130 of the plurality of openings 1120 is longer than the total width 1140 of the plurality of openings 1120. Openings 1120 are in fluid communication with the hollow interior of cutting tip 1100. Openings 1120 and the hollow interior lumen of cutting tip 1100 form a part of an aspiration pathway. Openings 1120 are generally circular (although they may be of any shape) and pierce the wall of cutting tip 1100. Each of the plurality of openings 1100 cut vitreous as the cutting tip 1100 is vibrated.

The arrow 1150 shows the direction that the tip 1100 is vibrated. In this case, the direction of vibration is generally rotational, twisting, or torsional and along or parallel to the width 1140 of the openings 1120 (and generally perpendicular or normal to the length 1130 of the openings 1120). When inserted into the posterior chamber of the eye and vibrated in this manner, the length 1130 of openings 1120 is moved perpendicular to the direction of vibration. In operation, an aspiration source, such as a pump, is fluidly coupled through the hand piece to the interior hollow lumen of cutting tip 1100. Vitreous is drawn into openings 1120 by this aspiration source. As vitreous is drawn into openings 1120, the cutting tip 1100 is vibrated, typically ultrasonically, so that the openings 1020 cut or shear the vitreous. During each stroke of vibration, vitreous drawn into openings 1120 is contacted by the edges of the opening 1120 along the length 1130.

Figure 12:
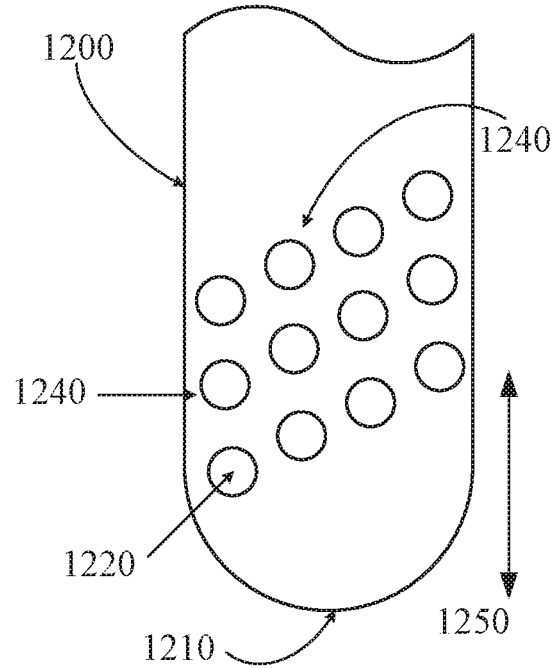
FIG. 12 is a perspective view of a cutting tip according to the principles of the present invention.

FIG. 12 is a front view of a cutting tip according to the principles of the present invention. Like the example of FIG. 11, a plurality of openings 1220 are located near the distal end 1210 of cutting tip 1200. The set of openings 1220 have a length 1230 and a width 1240. In this case, the total length 1230 of the plurality of openings 1220 is longer than the total width 1240 of the plurality of openings 1220. Openings 1220 are in fluid communication with the hollow interior of cutting tip 1200. Openings 1220 and the hollow interior lumen of cutting tip 1200 form a part of an aspiration pathway. Openings 1220 are generally circular (although they may be of any shape) and pierce the wall of cutting tip 1200. Each of the plurality of openings 1200 cut vitreous as the cutting tip 1200 is vibrated.

The arrow 1250 shows the direction that the tip 1100 is vibrated. In this case, the direction of vibration is generally rotational, twisting, or torsional and along or parallel to the width 1240 of the openings 1220 (and generally perpendicular or normal to the length 1230 of the openings 1220). When inserted into the posterior chamber of the eye and vibrated in this manner, the length 1230 of openings 1220 is moved perpendicular to the direction of vibration. In operation, an aspiration source, such as a pump, is fluidly coupled through the hand piece to the interior hollow lumen of cutting tip 1200. Vitreous is drawn into openings 1220 by this aspiration source. As vitreous is drawn into openings 1220, the cutting tip 1200 is vibrated, typically ultrasonically, so that the openings 1220 cut or shear the vitreous. During each stroke of vibration, vitreous drawn into openings 1220 is contacted by the edges of the opening 1220 along the length 1230.

While FIGS. 11 and 12 show two examples of an array of small openings, any number or arrangement of small openings can be utilized to effectively cut vitreous. For example, a single line of openings may be employed, or openings can be located around the periphery of the end of the cutting tip.

Figure 13:
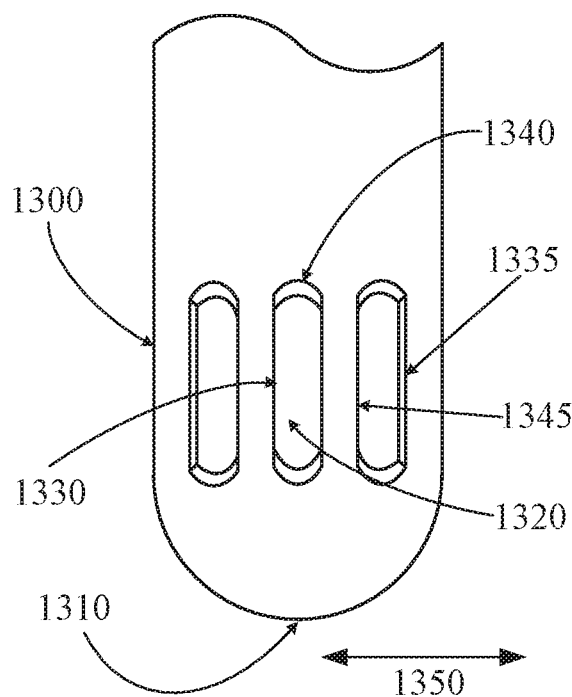
FIG. 13 is a perspective view of a cutting tip according to the principles of the present invention.

FIG. 13 is a front view of a cutting tip according to the principles of the present invention. In this example, cutting tip 1300 is a hollow shaft with a rounded distal end 1310. A plurality of openings 1320 are located near the distal end 1310 of cutting tip 1300. Openings 1320 each have a length 1330 and a width 1340. In this case, the length 1330 is longer than the width 1340. Openings 1320 are in fluid communication with the hollow interior of cutting tip 1300. Openings 1320 and the hollow interior lumen of cutting tip 1300 form a part of an aspiration pathway. Openings 1320 are each a slot-shaped opening that pierces the wall of cutting tip 1300. In this manner, a leading edge 1335 and trailing edge 1345 transverse the wall of cutting tip 1300. Both the leading edge 1335 and trailing edge 1345 of openings 1320 cut vitreous as the cutting tip 1300 is vibrated. In this way, the example of FIG. 13 with three slot-shaped openings is similar to that of FIG. 4 with a single slot shaped opening. As cutting tip 1300 is vibrated torsionally, the edges of the three slot-shaped openings contact and cut vitreous.

The arrow 1350 shows the direction that the tip 1300 is vibrated. In this case, the direction of vibration is generally torsional, twisting, or transversal along or parallel to the width 1340 of the openings 1320 (and generally perpendicular or normal to the length 1330 of the opening 1320). When inserted into the posterior chamber of the eye and vibrated in this manner, the length 1330 of openings 1320 is moved perpendicular to the direction of vibration. The edges 1335 and 1445 of the openings 1320 (i.e. the edges along the length 1330) are moved across vitreous in order to shear or cut it. In operation, an aspiration source, such as a pump, is fluidly coupled through the hand piece to the interior hollow lumen of cutting tip 1300. Vitreous is drawn into opening 1320 by this aspiration source. As vitreous is drawn into opening 1320, the cutting tip 1300 is vibrated, typically ultrasonically, so that the edges 1335 and 1345 along the length 1330 of openings 1320 cuts or shears the vitreous. During each stroke of vibration, vitreous drawn into openings 1320 is contacted by the edges 1335 and 1445 of openings 1320 along the length 1330. In this manner, the longer edges of openings 1320 are used to cut vitreous. Once cut, the vitreous is aspirated out of the eye through the hollow interior lumen of cutting tip 1300. The example of FIG. 28 is similar to that of FIG. 4. Instead of a single opening as shown in FIG. 4, a plurality of openings is shown in FIG. 28.

Figure 14:
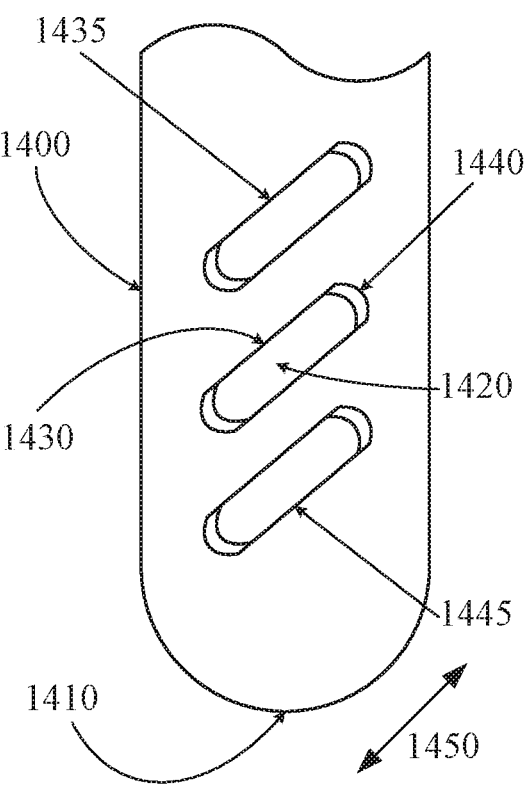
FIG. 14 is a perspective view of a cutting tip according to the principles of the present invention.

FIG. 14 is a front view of a cutting tip according to the principles of the present invention. In this example, cutting tip 1400 is a hollow shaft with a rounded distal end 1410. A plurality of openings 1420 are located near the distal end 1410 of cutting tip 1400. Openings 1420 each have a length 1430 and a width 1440. In this case, the length 1430 is longer than the width 1440. Openings 1420 are in fluid communication with the hollow interior of cutting tip 1400. Openings 1420 and the hollow interior lumen of cutting tip 1400 form a part of an aspiration pathway. Openings 1420 are each a slot-shaped opening that pierces the wall of cutting tip 1400. In this manner, a leading edge 1435 and trailing edge 1445 transverse the wall of cutting tip 1400. Both the leading edge 1435 and trailing edge 1445 of openings 1420 cut vitreous as the cutting tip 1400 is vibrated.

The arrow 1450 shows the direction that the tip 1400 is vibrated. In this case, the direction of vibration is generally diagonal, torsional, twisting, or transversal along or parallel to the width 1440 of the openings 1420 (and generally perpendicular or normal to the length 1430 of the opening 1420). When inserted into the posterior chamber of the eye and vibrated in this manner, the length 1430 of openings 1420 is moved perpendicular to the direction of vibration. The edges 1435 and 1445 of the openings 1420 (i.e. the edges along the length 1430) are moved across vitreous in order to shear or cut it. In operation, an aspiration source, such as a pump, is fluidly coupled through the hand piece to the interior hollow lumen of cutting tip 1400. Vitreous is drawn into opening 1420 by this aspiration source. As vitreous is drawn into opening 1420, the cutting tip 1400 is vibrated, typically ultrasonically, so that the edges 1435 and 1445 along the length 1430 of openings 1420 cuts or shears the vitreous. During each stroke of vibration, vitreous drawn into openings 1420 is contacted by the edges 1435 and 1445 of openings 1420 along the length 1430. In this manner, the longer edges of openings 1420 are used to cut vitreous. Once cut, the vitreous is aspirated out of the eye through the hollow interior lumen of cutting tip 1400. The example of FIG. 28 is similar to that of FIG. 4. Instead of a single opening as shown in FIG. 4, a plurality of openings is shown in FIG. 14.

Figure 15:
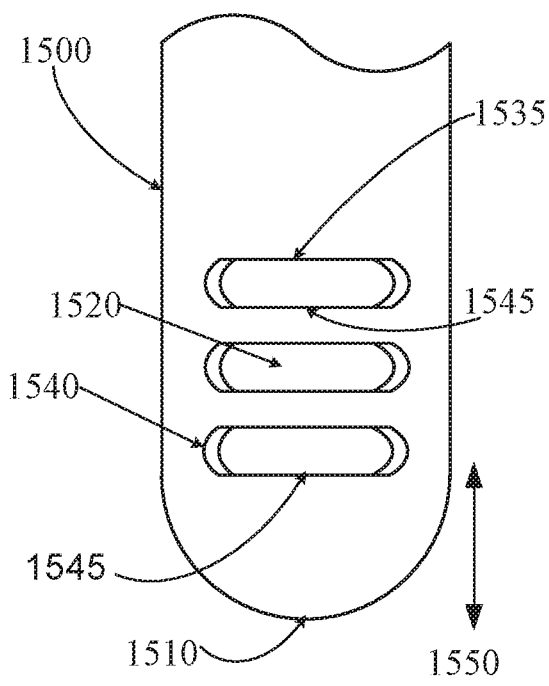
FIG. 15 illustrate three horizontal slot shaped ports in a cutting tip.

FIG. 15 illustrate three horizontal slot shaped ports 1520 in a cutting tip 1500. Compared to a single horizontal slot (e.g., as shown in FIGS. 6A-B), this arrangement of slots 1520 allows for greater interaction between the port edges 1535,1545 (indicated on the top port, but also includes the corresponding edges on the other two ports) and the vitreous during longitudinal actuation 1550. The additional ports may also increase the disruptive action on the collagen fibrils in response to torsional (cutting between edges 1540

(indicated on the bottom port, but also includes the corresponding edges on the other two ports) and vitreous) or both longitudinal and torsional ultrasonic cutter motion as well. Cutting tip 1500 may include a distal end 1510.

FIG. 17A is a perspective view of a cutting tip according to the principles of the present invention. FIG. 17B is a cross section view of the cutting tip shown in FIG. 17A. In this example, cutting tip 1700 is a hollow shaft with a rounded distal end 1710. A plurality of openings 1720 are located near the distal end 1710 of cutting tip 1700. Openings 1720 each have a length 1730 and a width 1740. In this case, the length 1730 is longer than the width 1740. Openings 1720 are in fluid communication with the hollow interior of cutting tip 1700. Openings 1720 and the hollow interior lumen of cutting tip 1700 form a part of an aspiration pathway. Openings 1720 are each a slot-shaped opening that pierces the wall of cutting tip 1700. In this manner, a leading edge 1735 and trailing edge 1745 transverse the wall of cutting tip 1700. Both the leading edge 1735 and trailing edge 1745 of openings 1720 cut vitreous as the cutting tip 1700 is vibrated. In this example, a raised structure or protrusion 1755 is located between two adjacent openings 1720. These structures 1755 alter the flow through openings 1720. In some instances, structures 1755 allow for more efficient flow through openings 1720.

The arrow 1750 shows the direction that the tip 1700 is vibrated. In this case, the direction of vibration is generally torsional, twisting, or transversal along or parallel to the width 1740 of the openings 1720 (and generally perpendicular or normal to the length 1730 of the opening 1720). When inserted into the posterior chamber of the eye and vibrated in this manner, the length 1730 of openings 1720 is moved perpendicular to the direction of vibration. The edges 1735 and 1745 of the openings 1720 (i.e. the edges along the length 1730) are moved across vitreous in order to shear or cut it. In operation, an aspiration source, such as a pump, is fluidly coupled through the hand piece to the interior hollow lumen of cutting tip 1700. Vitreous is drawn into opening 1720 by this aspiration source. As vitreous is drawn into opening 1720, the cutting tip 1733 is vibrated, typically ultrasonically, so that the edges 1735 and 1745 along the length 1730 of openings 1720 cuts or shears the vitreous. During each stroke of vibration, vitreous drawn into openings 1720 is contacted by the edges 1735 and 1745 of openings 1720 along the length 1730. In this manner, the longer edges of openings 1720 are used to cut vitreous. Once cut, the vitreous is aspirated out of the eye through the hollow interior lumen of cutting tip 1700. The example of FIGS. 17A and 17B is similar to that of FIG. 13. In FIGS. 17A and 17B, structures 1755 are located between openings 1720.

FIG. 18A is a perspective view of a cutting tip according to the principles of the present invention. FIG. 18B is a cross section view of the cutting tip shown is FIG. 18A. A plurality of openings 1820 are located near the distal end 1810 of cutting tip 1800. Openings 1820 are in fluid communication with the hollow interior of cutting tip 1800. Openings 1820 and the hollow interior lumen of cutting tip 1800 form a part of an aspiration pathway. Openings 1820 are generally circular (although they may be of any shape) and pierce the wall of cutting tip 1800. Each of the plurality of openings 1800 cut vitreous as the cutting tip 1800 is vibrated. In this example, a protrusion or structure 1855 is located between openings 1820. These structures 1855 alter the flow through openings 1820. In some instances, structures 1855 allow for more efficient flow through openings 1820.

The arrow 1850 shows the direction that the tip 1800 is vibrated. In operation, an aspiration source, such as a pump, is fluidly coupled through the hand piece to the interior hollow lumen of cutting tip 1800. Vitreous is drawn into openings 1820 by this aspiration source. As vitreous is drawn into openings 1820, the cutting tip 1800 is vibrated, typically ultrasonically, so that the openings 1820 cut or shear the vitreous. During each stroke of vibration, vitreous drawn into openings 1820 is contacted by the edges of the opening 1820.

Figure 16:
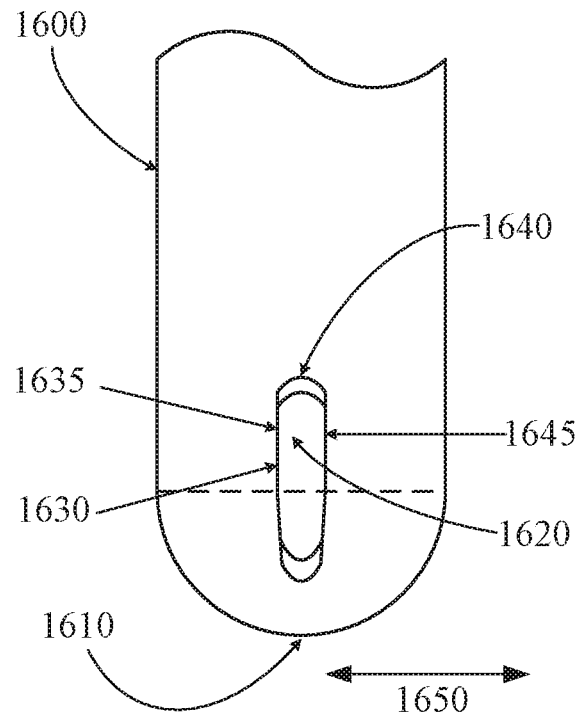
FIG. 16 is a perspective view of a cutting tip according to the principles of the present invention.

FIG. 16 is a front view of a cutting tip according to the principles of the present invention. The example of FIG. 16 is the same as the example of FIG. 4, except that the bottom portion of opening 1620 is located on the rounded distal end 1610 of cutting tip 1600 (as shown beneath the dotted line). In this case, approximately half of the opening 1620 is located on the rounded distal end 1610 while the other half (top half) is located on the wall of cutting tip 1600. In this example, the rounded distal end 1610 is spherical while the remainder of the cutting tip 1600 is cylindrical. Approximately half of the opening 1620 is located on the spherical (rounded distal end) portion of the cutting tip 1600 while the other half of opening 1620 is located on the cylindrical portion of cutting tip 1600.

In this example, cutting tip 1600 is a hollow shaft with a rounded (spherical) distal end 1610. An opening 1620 is located near the distal end 1610 of cutting tip 1600. Opening 1620 has a length 1630 and a width 1640. In this case, the length 1630 is longer than the width 1640. Opening 1620 is in fluid communication with the hollow interior of cutting tip 1600. Opening 1620 and the hollow interior lumen of cutting tip 1600 form a part of an aspiration pathway. Opening 1620 is a slot-shaped opening that pierces the wall of cutting tip 1600. In this manner, a leading edge 1635 and trailing edge 1645 transverse the wall of cutting tip 1600. Both the leading edge 1635 and trailing edge 1645 of opening 1620 cut vitreous as the cutting tip 1600 is vibrated.

The arrow 1650 shows the direction that the tip 1600 is vibrated. In this case, the direction of vibration is generally rotational, transversal, twisting, or torsional along or parallel to the width 1640 of the opening 1640 (and generally perpendicular or normal to the length 1630 of the opening 1620). When inserted into the posterior chamber of the eye and vibrated in this manner, the length 1630 of opening 1620 is moved perpendicular to the direction of vibration. The edges 1635 and 1645 of the opening 1620 (i.e. the edges along the length 1630) are moved across vitreous in order to shear or cut it. In operation, an aspiration source, such as a pump, is fluidly coupled through the hand piece to the interior hollow lumen of cutting tip 1600. Vitreous is drawn into opening 1620 by this aspiration source. As vitreous is drawn into opening 1620, the cutting tip 1600 is vibrated, typically ultrasonically, so that the edges 1635 and 1645 defined by the length 1630 of opening 1620 cuts or shears the vitreous. During each stroke of vibration, vitreous drawn into opening 1620 is contacted by the edges 1635 and 1645 of opening 1620 along the length 1630. In this manner, the longer edges of opening 1620 are used to cut vitreous. Once cut, the vitreous is aspirated out of the eye through the hollow interior lumen of cutting tip 1600.

Figure 19:
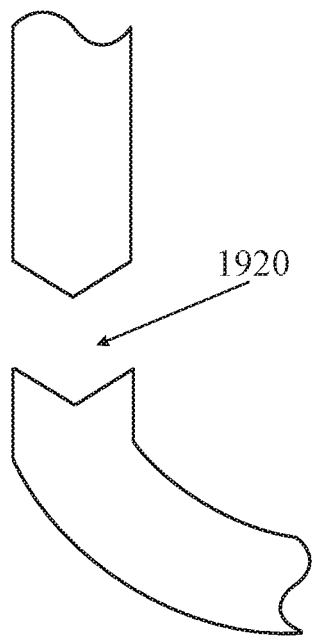
FIGS. 19-22 show various embodiments of a torturous flow path for a cutting tip's port hole.
Figure 20:
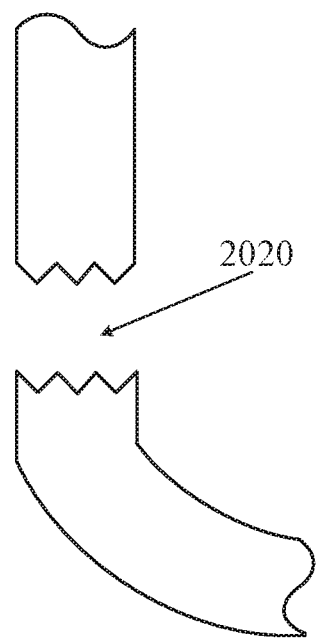
Figure 21:
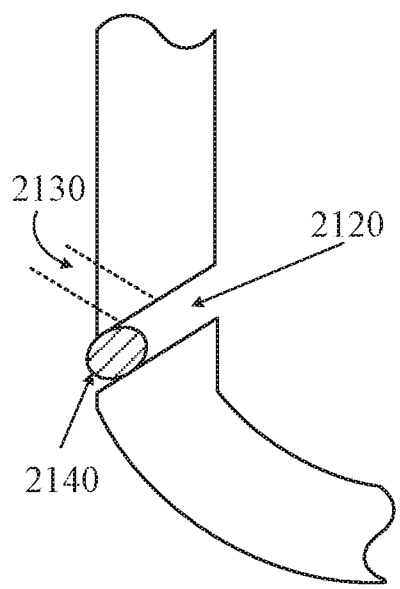
Figure 22:
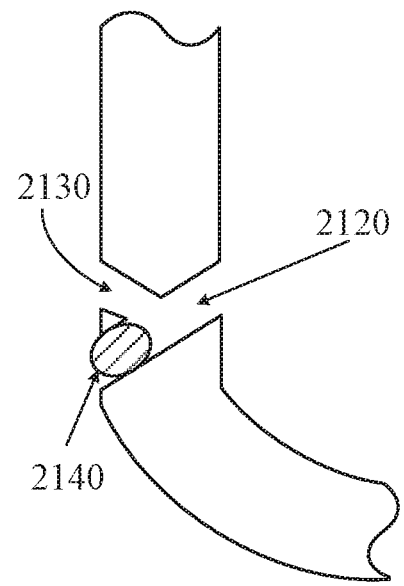

FIGS. 19-22 show various embodiments of a torturous flow path for a vitreous cutting tip's port hole. FIGS. 19-22 show a partial view of a side and distal end of a cutting tip. In some embodiments, the torturous flow path in the port's hole may be a jagged flow path 2020 (e.g., as seen in FIG. 20) or a reversing flow path 1920 (as seen in FIG. 19)). The reversing flow path could be created by drilling an off-axis hole 2120 (as seen in FIG. 21), spot-welding or otherwise sealing the external surface cutting tip, and drilling a second connecting off-axis hole 2130 (as seen in FIG. 22). Torsional ultrasonic power may amplify pressure differences and may break the vitreous under the resulting shear imparted on the vitreous fibers 2140 by the pressure differences. The torturous flow path may impart a greater shear stress than a simple through hole of similar dimensions. The torturous flow path additionally may allow for larger hole sizes while achieving the imparted shear stress over that which a smaller hole would provide.

Figures 23A, 23B:
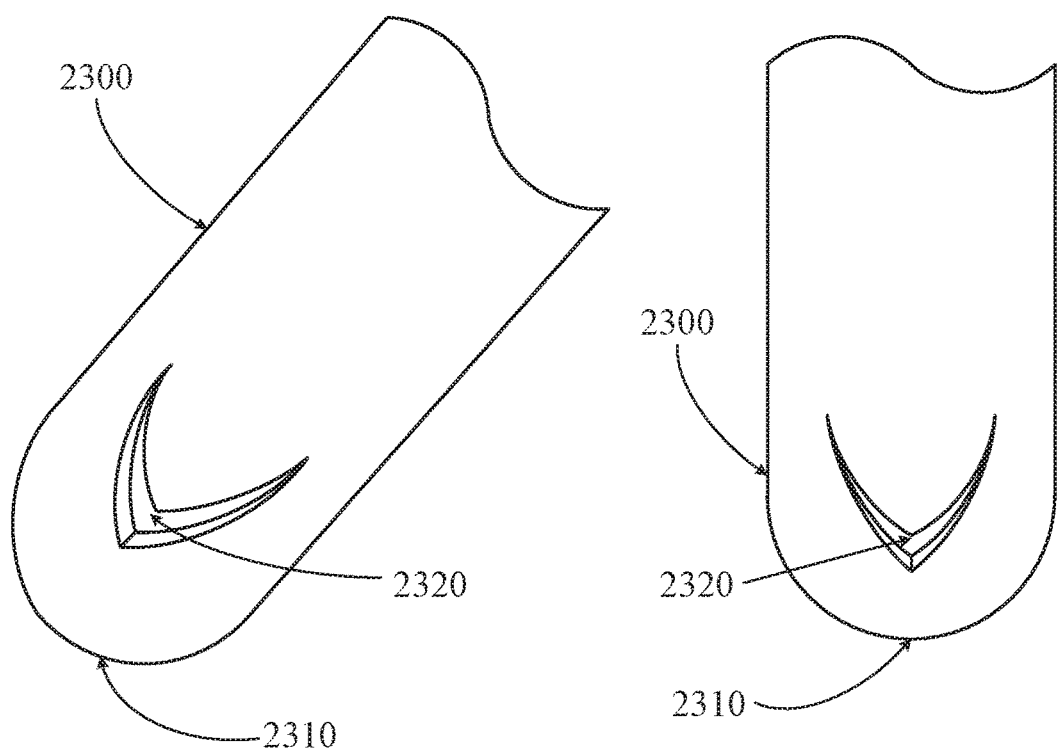
FIGS. 23A-B illustrates a chevron shaped cutting port in a cutting tip.

FIGS. 23A-B illustrates a chevron shaped cutting port 2320 in a cutting tip 2300. This configuration utilizes an internally-punched chevron to create a sharp hole on a vitreous cutting needle with an internal razor-like surface. Under torsional ultrasonic power and aspiration, the vitreous may be aspirated into the internal cavity where the razor-like surface and sharp hole cut the vitreous fibers with, for example, rotational motion. Shear forces imparted on the vitreous fluid by the complex surfaces provides additional cutting power. The punched-hole design provides a method to easily create an internal cutting surface as well as a sharp hole at the phaco needle exterior. Additionally, a torturous flow path may be created to provide further cutting power under, for example, flow and torsional power. The sharp surface edges and complex geometry may enhance vitreous cutting over a simple drilled hole. Cutting tip 2300 may include a distal end 2310.

Figures 24, 25:
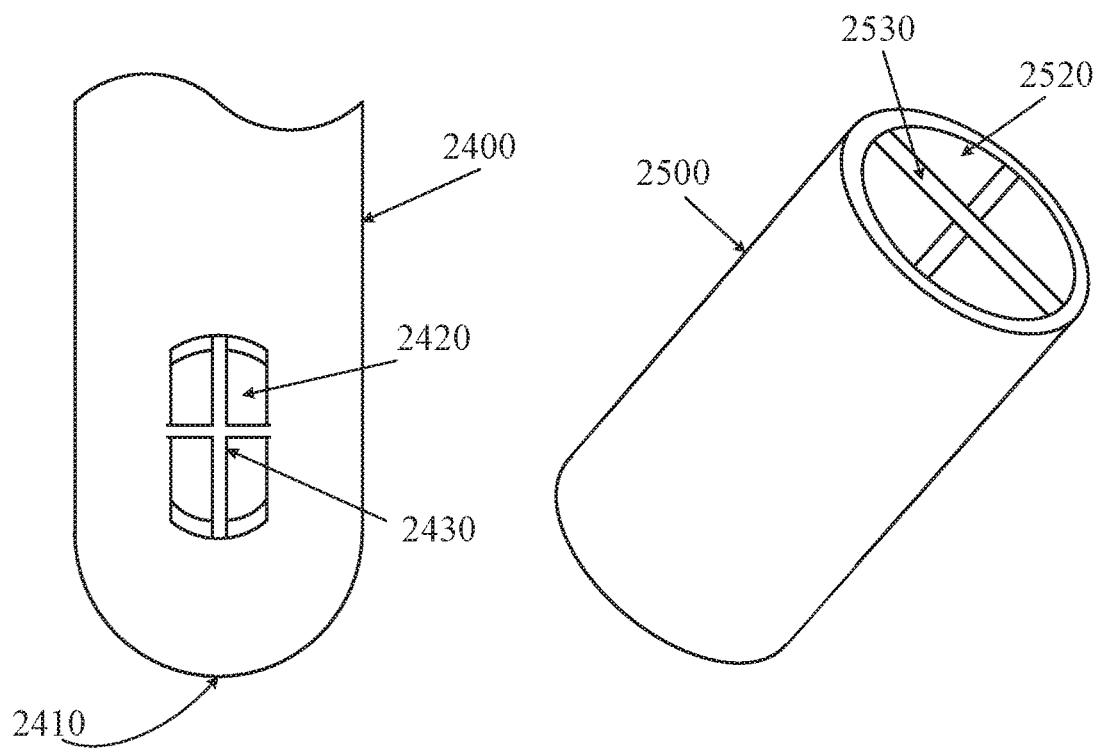
FIG. 24 is a perspective view of a cutting tip according to the principles of the present invention.
FIG. 25 illustrates an end facing port with a crisscrossing metal wire on a cutting tip.

FIG. 24 is a perspective view of a cutting tip according to the principles of the present invention. In this example, cutting tip 2400 is a hollow shaft with a rounded distal end 2410. An opening 2420 is located near the distal end 2410 of cutting tip 2400. Opening 2420 is in fluid communication with the hollow interior of cutting tip 2400. Opening 2420 and the hollow interior lumen of cutting tip 2400 form a part of an aspiration pathway. Opening 2420 is a generally vertical opening that pierces the wall of cutting tip 2400 as shown in FIG. 24. A pair of wires 2430 are placed in opening 2420. In this manner, the wires 2430 and edges of opening 2420 form cutting features. Both the wires 2430 and the edges of opening 2420 cut vitreous as the cutting tip 2400 is vibrated.

When inserted into the posterior chamber of the eye and vibrated in this manner, the opening 2420 is moved perpendicular to the direction of vibration. The wires 2430 and edges of the opening 2420 are moved across vitreous in order to shear or cut it. In operation, an aspiration source, such as a pump, is fluidly coupled through the hand piece to the interior hollow lumen of cutting tip 2400. Vitreous is drawn into opening 2420 by this aspiration source. As vitreous is drawn into opening 2420, the cutting tip 2400 is vibrated, typically ultrasonically, so that the wires 2430 and the edges defined by the opening 2420 cuts or shears the vitreous. During each stroke of vibration, vitreous drawn into opening 2420 is contacted by the wires 2430 and the edges of opening 2420. Once cut, the vitreous is aspirated out of the eye through the hollow interior lumen of cutting tip 2400.

FIG. 25 illustrates an end facing port 2520 with a crisscrossing metal wire 2530 on a cutting tip 2500. In a torsional ultrasonic vitreous cutter, the mechanism which "cuts" or "breaks" the vitreous fibers/strands in may be either or both: (a) "Cut"—High velocity physical impact of the metal against the vitreous "fibers", and/or (b) "Break"—High pressure that stretches the vitreous "fibers" longitudinally to its "breaking" point. For either: (a) a side port (traditional vitreous cutter), or (b) a distal port (open tube), the central area of the port opening may have the lowest velocity (for mechanism a) or the lowest pressure differential (mechanism b). Therefore, in the central area of the port, the "cut" or "break" may be performed with lower efficiency. By adding features like the crisscrossing metal wire 2530, the "cutting" or "breaking" action could be improved at the distal port 2520. A crisscrossing metal wire 2530 may similarly be added to the other concepts shown in this disclosure to increase cutting/breaking of the vitreous fibers during longitudinal/torsional actuation.

FIG. 26 illustrates a cross-shaped port 2620 on a cutting tip 2600. The port configuration may provide similar cutting edges in both longitudinal and torsional modes as other concepts described herein (e.g., as shown in FIG. 4A (vertical) and FIG. 6A (horizontal)). Collage fibrils may be cut equally well in either longitudinal or torsional mode.

FIG. 27 illustrates a V-shaped port 2720 on a cutting tip 2700. The V-shaped port 2720 may have similar properties as the ports shown in FIG. 5A and FIGS. 23A-23B.

FIG. 28 is a front view of a cutting tip according to the principles of the present invention. In this example, cutting tip 2800 is a hollow shaft with a rounded distal end 2810. An opening 2820 is located near the distal end 2810 of cutting tip 2800. Opening 2820 is in fluid communication with the hollow interior of cutting tip 2800. Opening 2820 and the hollow interior lumen of cutting tip 2800 form a part of an aspiration pathway. Opening 2820 is generally oval shaped as shown in FIG. 28 and pierces the wall of cutting tip 2800. Oval-shaped opening 2820 has a plurality of edges that cut vitreous as the cutting tip 2800 is vibrated.

When inserted into the posterior chamber of the eye and vibrated, the edges of the opening 2820 are moved across vitreous in order to shear or cut it. In operation, an aspiration source, such as a pump, is fluidly coupled through the hand piece to the interior hollow lumen of cutting tip 2800. Vitreous is drawn into opening 2820 by this aspiration source. As vitreous is drawn into opening 2820, the cutting tip 2800 is vibrated, typically ultrasonically, so that the edges defined by the opening 2820 cuts or shears the vitreous. During each stroke of vibration, vitreous drawn into opening 2820 is contacted by the edges of opening 2820. In this manner, the edges of opening 2820 are used to cut vitreous. Once cut, the vitreous is aspirated out of the eye through the hollow interior lumen of cutting tip 2800. The example of FIG. 28 is very similar to that of FIG. 4. In FIG. 28, the oval-shaped opening 2820 produces slightly different flow characteristics as vitreous is cut and aspirated.

From the above, it may be appreciated that the present invention provides an improved cutting tip for the removal of vitreous. The present invention provides a cutting tip with an opening configured to cut vitreous when the cutting tip is vibrated ultrasonically. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An ultrasonic cutting tip comprising:
  a hollow shaft with a proximal end and a distal end, the proximal end configured to be attached to an ultrasonic hand piece configured to produce torsional vibration, of the hollow shaft, along a direction of vibration, and the distal end having a smooth continuous surface, the hollow shaft having an longitudinal axis that extends through an interior lumen of the hollow shaft, wherein the torsional vibration comprises back and forth motion of the hollow shaft that is perpendicular to the longitudinal axis of the hollow shaft;

an opening located near the distal end of the hollow shaft, the opening having a width and a length, the length being longer than the width;

wherein the width of the opening is oriented along the direction of vibration and perpendicular to the longitudinal axis of the hollow shaft, wherein the torsional vibration of the hollow shaft is further parallel to the width of the opening, wherein the torsional vibration of the hollow shaft is configured to cut tissue as it enters the opening without additional cutting mechanisms inside the hollow shaft.

2. The ultrasonic cutting tip of claim 1 wherein the opening is slot-shaped and traverses a wall of the hollow shaft at an oblique angle so as to form a first edge and a second edge along the length of the opening, and further wherein the length of the opening is oriented parallel to the longitudinal axis of the hollow shaft, wherein a wall of the hollow shaft on one side of the opening curves inward such that the first edge, on one side of the opening, is closer to the longitudinal axis of the hollow shaft than the second edge, on an opposing side of the opening, wherein a distance between the first edge and the second edge forms the width of the opening.

3. The ultrasonic cutting tip of claim 1 wherein the opening is slot-shaped and traverses a wall of the hollow shaft at a right angle so as to form a leading edge and a trailing edge along the length of the opening, and further wherein the length of the opening is oriented parallel to the longitudinal axis of the hollow shaft.

4. The ultrasonic cutting tip of claim 3 further comprising two additional slot-shaped openings that each traverse the wall of the hollow shaft at a right angle, and further wherein a length of each of the additional slot-shaped openings is oriented parallel to the longitudinal axis of the hollow shaft.

5. The ultrasonic cutting tip of claim 4 further comprising a raised structure located between two of the slot-shaped openings.

6. The ultrasonic cutting tip of claim 3 wherein the distal end of the hollow shaft is spherical and the slot-shaped opening traverses the wall of the hollow shaft such that a portion of the slot-shaped opening traverses the spherical distal end.

7. The ultrasonic cutting tip of claim 1 further comprising an array of openings, the opening and the array of openings each traversing a wall of the hollow shaft, the opening and the array of openings being arranged near a distal end of the hollow shaft.

8. The ultrasonic cutting tip of claim 7 further comprising a raised structure located between two of the openings in the array of openings.

9. The ultrasonic cutting tip of claim 1 wherein the opening is oval-shaped.

10. The ultrasonic cutting tip of claim 1 further comprising a pair of wires located in the opening.

11. An ultrasonic cutting instrument comprising:
an ultrasonic hand piece, the ultrasonic hand piece configured to produce torsional vibration, of the hollow shaft, along a direction of vibration; and
a cutting tip comprising: a hollow shaft with a proximal end and a distal end, the proximal end configured to be attached to the ultrasonic hand piece and the distal end having a smooth continuous surface; an opening located near the distal end of the hollow shaft, the opening having a width and a length, the length being longer than the width, the hollow shaft having a longitudinal axis that extends through an interior lumen of the hollow shaft, wherein the ultrasonic handpiece is configured to produce torsional vibration of the hollow shaft that comprises back and forth motion of the hollow shaft that is perpendicular to the longitudinal axis of the hollow shaft;

wherein the width of the opening is oriented along the direction of vibration and perpendicular to the longitudinal axis of the hollow shaft;

wherein the torsional vibration of the hollow shaft is further parallel to the width of the opening; and wherein the torsional vibration of the hollow shaft is configured to cut tissue as it enters the opening without additional cutting mechanisms inside the hollow shaft.

12. The ultrasonic cutting tip of claim 11 wherein the opening is slot-shaped and traverses a wall of the hollow shaft at an oblique angle so as to form a first edge and a second edge along the length of the opening, and further wherein the length of the opening is oriented parallel to the longitudinal axis of the hollow shaft, wherein a wall of the hollow shaft on one side of the opening curves inward such that the first edge, on one side of the opening, is closer to the longitudinal axis of the hollow shaft than the second edge, on an opposing side of the opening, wherein a distance between the first edge and the second edge forms the width of the opening.

13. The ultrasonic cutting tip of claim 11 wherein the opening is slot-shaped and traverses a wall of the hollow shaft at a right angle so as to form a leading edge and a trailing edge along the length of the opening, and further wherein the length of the opening is oriented parallel to the longitudinal axis of the hollow shaft.

14. The ultrasonic cutting tip of claim 13 further comprising two additional slot-shaped openings that each traverse the wall of the hollow shaft at a right angle, and further wherein a length of each of the additional slot-shaped openings is oriented parallel to the longitudinal axis of the hollow shaft.

15. The ultrasonic cutting tip of claim 14 further comprising a raised structure located between two of the slot-shaped openings.

16. The ultrasonic cutting tip of claim 13 wherein the distal end of the hollow shaft is spherical and the slot-shaped opening traverses the wall of the hollow shaft such that a portion of the slot-shaped opening traverses the spherical distal end.

17. The ultrasonic cutting tip of claim 11 further comprising an array of openings, the opening and the array of openings each traversing a wall of the hollow shaft, the opening and the array of openings being arranged near a distal end of the hollow shaft.

18. The ultrasonic cutting tip of claim 17 further comprising a raised structure located between two of the openings in the array of openings.

19. The ultrasonic cutting tip of claim 11 wherein the opening is oval-shaped.

20. The ultrasonic cutting tip of claim 11 further comprising a pair of wires located in the opening.

* * * * *